United States Patent
Nakabayashi

(12) 
(10) Patent No.: US 7,619,415 B2
(45) Date of Patent: Nov. 17, 2009

(54) MAGNETIC RESONANCE IMAGING APPARATUS, RF COIL SYSTEM, AND MAGNETIC RESONANCE IMAGING METHOD

(75) Inventor: Kazuto Nakabayashi, Nasushiobara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 0 days.

(21) Appl. No.: 12/078,753

(22) Filed: Apr. 4, 2008

(65) Prior Publication Data

US 2008/0246477 A1 Oct. 9, 2008

(30) Foreign Application Priority Data

Apr. 6, 2007 (JP) ............................. 2007-100623
Mar. 14, 2008 (JP) ............................. 2008-066365

(51) Int. Cl.
*G01V 3/00* (2006.01)

(52) U.S. Cl. ...................... 324/318; 324/322

(58) Field of Classification Search ......... 324/300–322; 600/407–445
See application file for complete search history.

(56) References Cited

U.S. PATENT DOCUMENTS

| 5,384,536 | A | 1/1995 | Murakami et al. |
| 5,666,055 | A * | 9/1997 | Jones et al. ................. 324/318 |
| 6,362,622 | B1 | 3/2002 | Stauber et al. |
| 7,391,214 | B2 * | 6/2008 | Adachi ....................... 324/318 |
| 2004/0116801 | A1 * | 6/2004 | Konings et al. ............. 600/411 |
| 2007/0182409 | A1 * | 8/2007 | Varjo .......................... 324/304 |

FOREIGN PATENT DOCUMENTS

JP  2001-346775  12/2001

* cited by examiner

*Primary Examiner*—Brij B Shrivastav
(74) *Attorney, Agent, or Firm*—Nixon & Vanderhye PC

(57) ABSTRACT

A magnetic resonance imaging apparatus has at least one RF coil and a data processing control unit. The RF coil generates unique information receives a nuclear magnetic resonance signal, and wirelessly transmits the received nuclear magnetic resonance signal and the unique information. The data processing control unit receives the wirelessly transmitted nuclear magnetic resonance signal and the unique information, and generates image data based on the nuclear magnetic resonance signal in accordance with the unique information.

17 Claims, 10 Drawing Sheets

| UNIQUE INFORMATION | ATTRIBUTE INFORMATION | | | | |
|---|---|---|---|---|---|
| | USE | TYPE | SHAPE | | |
| | | | NUMBER | ARRANGEMENT | |
| FIRST RF COIL | CHEST | TRANSMISSION/ RECEPTION USE | 2 | ONE ROW IN x-DIRECTION | |
| SECOND RF COIL | SPINE | TRANSMISSION/ RECEPTION USE | 16 | x-DIRECTION X z-DIRECTION = 4 X 4 | |
| ⋮ | ⋮ | ⋮ | ⋮ | ⋮ | |

FIG. 2

MAGNETIC RESONANCE IMAGING APPARATUS, RF COIL SYSTEM, AND MAGNETIC RESONANCE IMAGING METHOD

BACKGROUND OF THE INVENTION

1. Field of the Invention

The present invention relates to a magnetic resonance imaging (MRI) apparatus that magnetically excites an atomic nuclear spin of an object by using a radio frequency (RF) signal having a Larmor frequency and reconstructs an image from a nuclear magnetic resonance (NMR) signal produced with the excitation and to an RF coil system for use therein. In particular, the present invention relates to an MRI apparatus that wirelessly transmits a received signal, an RF coil system for use therein, and an MRI method.

2. Description of the Related Art

MRI is an imaging method of magnetically exciting an atomic nuclear spin of an object placed in a static magnetic field by using an RF signal having a Larmor frequency and reconstructing an image from an NMR signal produced with the excitation.

The number of RF coils for receiving an NMR signal in recent MRI apparatuses has a tendency to be increased. In known MRI apparatuses, NMR signals are received using all RF coils, and an image is generated by the received NMR signals. As a result, an MRI apparatus has reception channels of the same number as the RF coils and generates the image by data processing of a reception signal corresponding to each of the reception channels.

However, imaging needs data related to processing the reception channels, so the length of time required for the processing can be long. An increase in the processing time results in an increase in time required for obtaining the image of a patient as the object, thus putting a heavy load on the patient.

One known technique for storing attribute information in RF coils to locally collect necessary data using only the RF coils is disclosed (see, for example, Japanese Patent Application Publication No. 2001-346775). In this technique, the RF coils can be identified based on the attribute information, and necessary data can be selectively collected using a specific RF coil. This reduces the amount of data processing and the length of processing time.

RF coils used in a known MRI apparatus are electrically connected to a controller with a conductive cable, and reception signals output from the RF coils and control signals are transmitted via the cables. However, the cable not only hinders the placement of the patient on a table-top of a bed system but also incurs the risk of burning the patient by RF induction caused when the patient comes into contact with the cable.

One approach to this problem is a technique for transmitting a signal without electrically connecting an RF coil to a controller. One example of the technique is to convert a signal output from the RF coil from electrical to optical form. For this technique, although it is necessary to connect the RF coil to an optical cable, the optical cable used in signal transmission can be relatively thin. The use of an optical cable in signal transmission can reduce the risk of producing a burn because there is no electrical contact with a body of the patient.

Another example of means of transmitting a signal using non-electrical connection is a technique for converting a signal into an electromagnetic wave and performing wireless transmission from an RF coil to a controller. That is, a technique for converting an electrical signal output from an RF coil used for signal reception in obtaining an image into a radio wave and transmitting it to the controller is discussed.

However, when the electrical signal output from the RF coil is transmitted as a radio wave to the controller, it is difficult for an MRI apparatus that can position a plurality of RF coils in the vicinity of the patient to automatically identify an RF coil positioned for collecting data at the controller.

For example, a plurality of RF coils typically exists in an imaging room where the MRI apparatus is set. During imaging, an RF coil corresponding to an imaging target section is positioned above or adjacent to the patient. However, RF coils that are not positioned above or not adjacent to the patient also receive signals. Signals from such RF coils are unnecessary signals from sections other than the imaging target section of the patient. It is thus preferred that the signals from the RF coils that are not positioned above nor adjacent to the object be removed. However, the controller cannot identify from which RF coil the collected data has come, so it is difficult to remove the unnecessary data.

Because of this, it is necessary to wirelessly transmit signals received in all RF coils to the controller and extract only data required for diagnosis after the completion of data processing. However, this leads to an increase in unnecessary data processing.

SUMMARY OF THE INVENTION

In view of the above circumstances, it is a purpose of the present invention to provide a magnetic resonance imaging apparatus, an RF coil system and a magnetic resonance imaging method capable of generating an image with a reduced amount of data processing by selectively exploiting data from an RF coil for use in data collection.

In view of the above circumstances, another purpose of the present invention is to provide a magnetic resonance imaging apparatus, an RF coil system and a magnetic resonance imaging method capable of identifying an RF coil that is the source of each reception data based on attribute information, such as arrangement of coil elements, and thus appropriately perform a image correction such as a luminance correction by using a correction value assigned for each RF coil.

To solve the above-described problems, the present invention provides a magnetic resonance imaging apparatus comprising: at least one RF coil that generates unique information, receives a nuclear magnetic resonance signal, and wirelessly transmits the received nuclear magnetic resonance signal and the unique information; and a data processing control unit configured to receive the wirelessly transmitted nuclear magnetic resonance signal and the unique information, and to generate image data based on the nuclear magnetic resonance signal in accordance with the unique information.

To solve the above-described problems, the present invention provides an RF coil system comprising: a unique information generating unit configured to generate unique information; a coil element configured to receive a nuclear magnetic resonance signal; and a transmitting unit wirelessly transmit the unique information and the nuclear magnetic resonance signal.

To solve the above-described problems, the present invention provides a magnetic resonance imaging method comprising: a receiving step of generating unique information for each RF coil, generating a nuclear magnetic resonance signal for each of one or more coil elements constituting the RF coil, and receiving the unique information and the nuclear magnetic resonance signal; a transmitting step of wirelessly transmitting the nuclear magnetic resonance signal and the unique information received in the receiving step; and a data processing step of receiving the nuclear magnetic resonance signal and the unique information wirelessly transmitted in the transmitting step and generating image data based on the nuclear magnetic resonance signal in accordance with the unique information.

BRIEF DESCRIPTION OF THE DRAWINGS

FIG. 2 illustrates an example of a correspondence table of unique information on RF coils and attribute information on the RF coils;

DESCRIPTION OF THE PREFERRED EMBODIMENTS

Embodiments of an MRI apparatus, an RF coil system, and an MRI method will be described with reference to the accompanying drawings.

Figure 1:
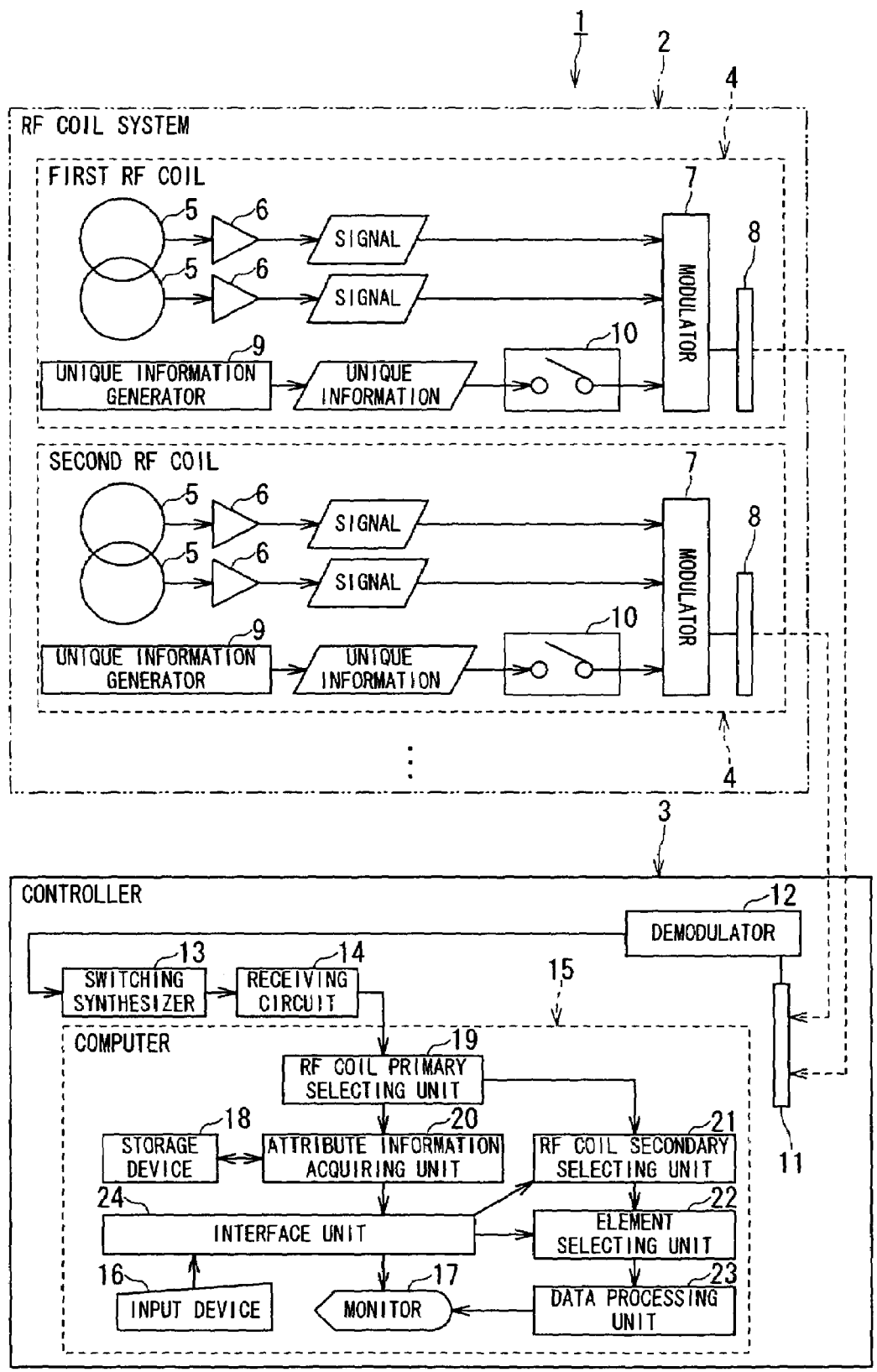
FIG. 1 is a block diagram of an MRI apparatus according to an embodiment of the present invention.

FIG. 1 is a block diagram of an MRI apparatus according to an embodiment of the present invention.

FIG. 1 illustrates an MRI apparatus 1 according to the present embodiment. The MRI apparatus 1 has an RF coil system 2 and a controller 3. The RF coil system 2 and the controller 3 are located in a shielded room (not shown). The RF coil system 2 has a function of receiving an NMR signal produced with the excitation of an atomic nuclear spin within an object (not shown) caused by an RF signal and a function of wirelessly transmitting the received NMR signal to the controller 3. The RF coil system 2 includes a plurality of RF coils 4 and has a function of wirelessly transmitting unique information (first RF coil, second RF coil, . . . ) on the RF coils 4, such as a coil identification (ID), together with NMR signals from the RF coils 4 to the controller 3.

Each of the RF coils 4 includes a plurality of coil elements 5. In the example shown in FIG. 1, each of the RF coils 4 includes two coil elements 5. Each of the coil elements 5 receives respectively corresponding NMR signals. Each of the coil elements 5 is connected to an amplifier 6 and is configured to output a reception signal from the amplifier 6. The output sides of the amplifiers 6 belonging to the same RF coil 4 are connected to a modulator 7. The output side of the modulator 7 is connected to a signal transmitting antenna 8. A reception signal from each of the coil elements 5 is modulated into a corresponding specific frequency by the modulator 7, and then wirelessly transmitted from the signal transmitting antenna 8 to the controller 3.

At least one of the RF coils 4 includes a unique information generator 9. Preferably, as illustrated in FIG. 1, all the RF coils 4 may include the respective unique information generators 9. The output side of each of the unique information generators 9 is connected to the modulator 7. The unique information generator 9 has a function of generating unique information for use in identifying a corresponding RF coil 4 and outputting the unique information as a unique information signal to the modulator 7.

The output side of the unique information generator 9 can be provided with a switch 10 as needed. The unique information generator 9 is configured to output the unique information signal to the modulator 7 when the switch 10 is in an ON state. The unique information signal output to the modulator 7 is frequency-modulated. The frequency-modulated signal is superposed on a reception signal and wirelessly transmitted from the signal transmitting antenna 8 to the controller 3. That is, the provision of the switch 10 to the unique information generator 9 enables the unique information signal to be wirelessly transmitted from only an RF coil 4 corresponding to the switch 10 being in the ON state.

Note that a frequency band of a transmit frequency of the unique information signal is set at a band different from the frequency band of a transmit frequency of an MR reception signal. Modulating the unique information signal and the MR reception signal into different frequencies enables them to be identified and separated from each other at the reception side of the wireless transmission.

The controller 3 has a function of generating an MR image by receiving an NMR signal wirelessly transmitted from the RF coil system 2 and performing data processing. The controller 3 includes a signal receiving antenna 11, a demodulator 12, a switching synthesizer 13, a receiving circuit 14, and a computer 15. The computer 15 includes an input device 16, a monitor 17, and a storage device 18. By executing a program stored in a storage device 18 using an arithmetical device such as a central processing unit (CPU), the computer 15 functions as an RF coil primary selecting unit 19, an attribute information acquiring unit 20, an RF coil secondary selecting unit 21, an element selecting unit 22, a data processing unit 23, and an interface unit 24. The controller 3 may include a circuit for performing all or part of the functions of the computer 15.

The signal receiving antenna 11 is an antenna for receiving a reception signal and the unique information signal that are wirelessly transmitted from the signal transmitting antenna 8.

The demodulator 12 has a function of returning the frequency of each of the reception signal and the unique information signal received through the signal receiving antenna 11 to the original frequency, which is the frequency before the frequency modulation is performed, by demodulating it and a function of outputting the demodulated reception signal and the unique information signal superposed thereon to the switching synthesizer 13.

The switching synthesizer 13 can be disposed as needed. The switching synthesizer 13 has a function of reception signals for use in image generation corresponding to a desired number of channels by performing desired dividing and/or combining processing on reception signals from the coil elements 5 belonging to the same RF coil 4 or from the coil elements 5 of the different RF coils 4 and of outputting the generated reception signals to the receiving circuit 14.

The receiving circuit 14 has the function of generating digitized reception data by performing desired a signal processing, such as a detection or an analog to digital (A/D) conversion, on the reception signals acquired from the switching synthesizer 13 and of outputting the generated reception data to the computer 15. The reception data is generated for each of the coil elements 5 of the RF coil 4. The reception data includes the unique information as the unique information signal on the RF coil 4.

The storage device 18 stores the unique information on the RF coil 4 and attribute information on the RF coil 4 in association with each other. Examples of the attribute information include information indicating a use (e.g., for a head, for a chest, for a leg, or the like), information indicating a type (e.g., a shared use of transmission/reception, a reception use), information indicating a shape (e.g., the shape of the RF coil 4 itself, the number and arrangement of coil elements 5), and information indicating a location on the RF coil 4.

FIG. 2 illustrates one example of a correspondence table of the unique information on the RF coils 4 and the attribute information on the RF coils 4.

As illustrated in FIG. 2, for example, "First RF coil" as the unique information is associated with the attribute information such as "chest" as the use, "transmission/reception use" as the type, "2" as the number of coil elements 5, and "one row in x-direction".

The RF coil primary selecting unit 19 of the computer 15 illustrated in FIG. 1 has a function of receiving reception data with unique information and reception data without unique information from the receiving circuit 14 and a function of selecting only the reception data with the unique information and of outputting the unique information to the attribute information acquiring unit 20 and the reception data with the unique information to the RF coil secondary selecting unit 21.

The attribute information acquiring unit 20 has a function of outputting, to the interface unit 24, attribute information (unique information and attribute information) acquired by referring to the storage device 18 based on the unique information input from the RF coil primary selecting unit 19.

The RF coil secondary selecting unit 21 has a function of extracting reception data regarding a specific RF coil 4 from reception data with unique information input from the attribute information acquiring unit 20 based on the selection information on the RF coil 4 input from the interface unit 24 and of outputting the extracted reception data to the element selecting unit 22.

The element selecting unit 22 has a function of extracting reception data regarding a specific coil element 5 from the reception data regarding the specific RF coil 4 input from the RF coil secondary selecting unit 21 based on selection information on the coil element 5 input from the interface unit 24 and a function of outputting the extracted reception data to the data processing unit 23. Because identifying information on the coil element 5 is attached to the reception data in advance, although a plurality of coil elements 5 belonging to the same RF coil 4 shares common unique information, as long as the RF coil 4 is identified, it can be identified which coil element 5 corresponds to the reception data.

The data processing unit 23 has a function of generating image data by performing image reconstruction processing, such as a Fourier transform processing, and other necessary image processing on reception data input from the element selecting unit 22 and a function of displaying the generated image data on the monitor 17.

The interface unit 24 has a function of displaying the attribute information on the RF coil 4 input from the attribute information acquiring unit 20 on the monitor 17, a function of receiving selection instructing information on the RF coil 4 and selection instructing information on the coil element 5 from the input device 16 and of outputting them to the RF coil secondary selecting unit 21 and the element selecting unit 22, respectively, and a function of displaying the selection information on the RF coil 4 and the selection information on the coil element 5 on the monitor 17.

That is, the computer 15 has a function of primarily selecting only one or more RF coils 4 (reception data with unique information on the RF coils 4) from among all the RF coils 4, a function of secondarily selecting only a specific RF coil 4 (reception data with unique information on the specific RF coil 4) from among the primarily selected RF coils 4, and a function of selecting only a specific coil element 5 (reception data from the specific coil element 5) from the secondarily selected RF coil 4. Therefore, only the extracted reception data is a target for data processing, so an increase in the amount of data processing can be suppressed. In such a way, the computer 15 can extract reception data after data collection.

The use of switching of the switch 10 of the unique information generator 9 in the RF coil 4 enables necessary reception data to be received before data collection such that the reception data can be identified.

The computer 15 can identify the RF coil 4 that is the source of received reception data based on the attribute information corresponding to the unique information on the RF coil 4 received with the reception data. Therefore, the computer 15 can appropriately perform an image correction such as a luminance correction by using a correction value assigned for each of the RF coils 4.

Figure 3:
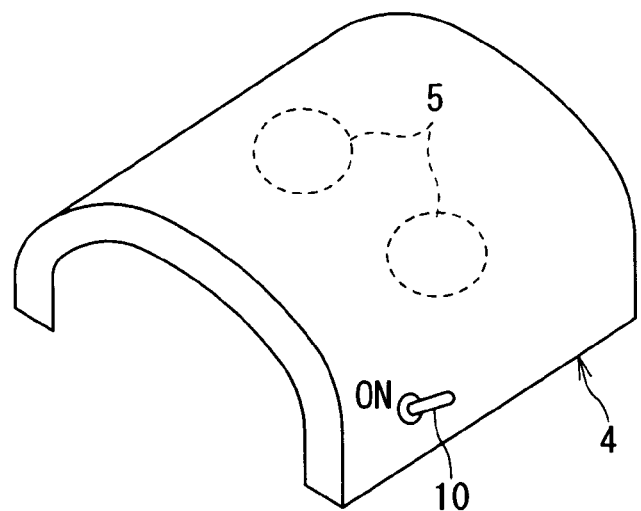
FIG. 3 illustrates a configuration example of a switch of a unique information generator set on an RF coil shown in FIG. 1.

FIG. 3 illustrates a configuration example of the switch 10 of the unique information generator 9 set on the RF coil 4 shown in FIG. 1.

As illustrated in FIG. 3, the RF coil 4 can be U-shaped in cross section and incorporate two coil elements 5, for example. The switch 10 of the unique information generator 9 can be constructed as, for example, a lever set on an outer surface of the RF coil 4 such that an operator can switch between on and off settings. Switching the switch 10 to the ON state in advance of obtaining an image enables unique information on an RF coil 4 indicating that the RF coil 4 is used for data collection to be wirelessly transmitted.

Figure 4:
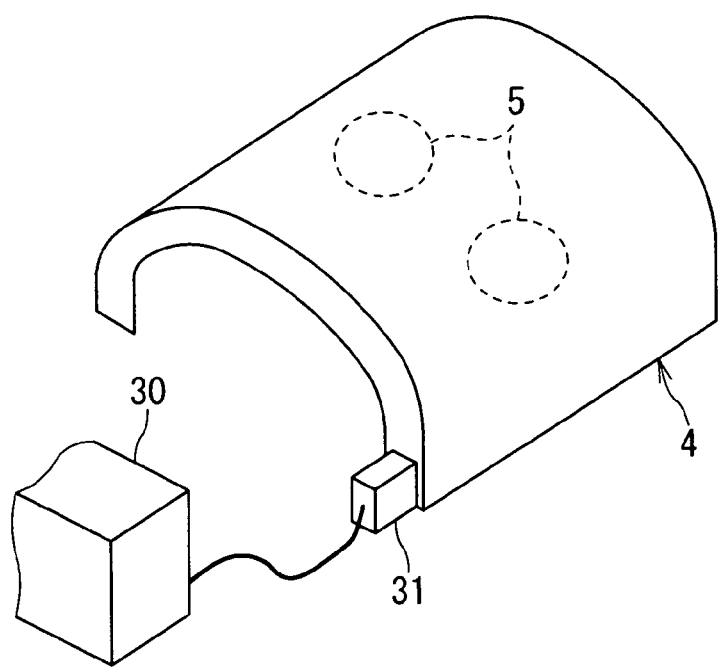
FIG. 4 illustrates another configuration example of the switch of the unique information generator set on the RF coil shown in FIG. 1.

FIG. 4 illustrates another configuration example of the switch 10 of the unique information generator 9 set on the RF coil 4 shown in FIG. 1.

As illustrated in FIG. 4, the RF coil 4 can be U-shaped in cross section and incorporate two coil elements 5, for example. In the case of the RF coil 4 operating wirelessly, power is supplied to the RF coil 4 from an internal battery, not through a cable. The internal battery may preferably be charged when the RF coil 4 is not used. Thus, a battery charger 30 for charging the battery incorporated in the RF coil 4 is disposed in an imaging room where the MRI apparatus 1 is set.

Further, switching operation of the switch 10 of the unique information generator 9 between on and off settings can be determined by whether or not a connector 31 of the battery charger 30 is connected to the battery incorporated in the RF coil 4. More specifically, when the connector 31 of the battery charger 30 is connected to the battery incorporated in the RF coil 4, which means that the RF coil 4 is not used, the switch 10 of the unique information generator 9 is in the OFF state and the unique information on the RF coil 4 is not wirelessly transmitted. In contrast, when the connector 31 of the battery charger 30 is detached from the RF coil 4, the switch 10 of the unique information generator 9 is in the ON state, so the unique information on the RF coil 4 is wirelessly transmitted.

Figure 5:
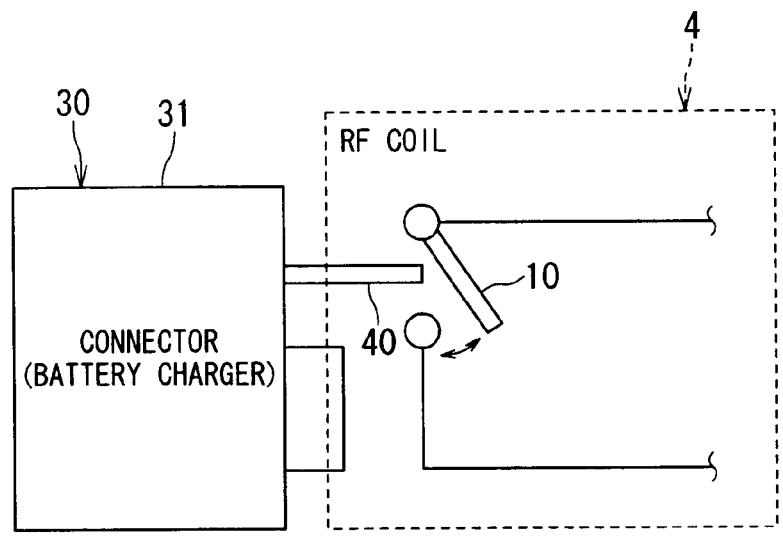
FIG. 5 illustrates an example of the switch of the unique information generator, the switch having a mechanical structure that is automatically turned off in accordance with a state of a connector of a buttery charger shown in FIG. 4.

FIG. 5 illustrates one example of the switch 10 of the unique information generator 9, the switch 10 having a mechanical structure that is automatically turned off in accordance with a state of the connector 31 of the battery charger 30 shown in FIG. 4.

As illustrated in FIG. 5, when the connector 31 of the battery charger 30 is provided with, for example, a switching protrusive bar 40 configured to mechanically open the switch 10 of the unique information generator 9, the switch 10 of the unique information generator 9 set on the RF coil 4 can be automatically switched to the OFF state by connection of the connector 31 of the battery charger 30.

Figure 6:
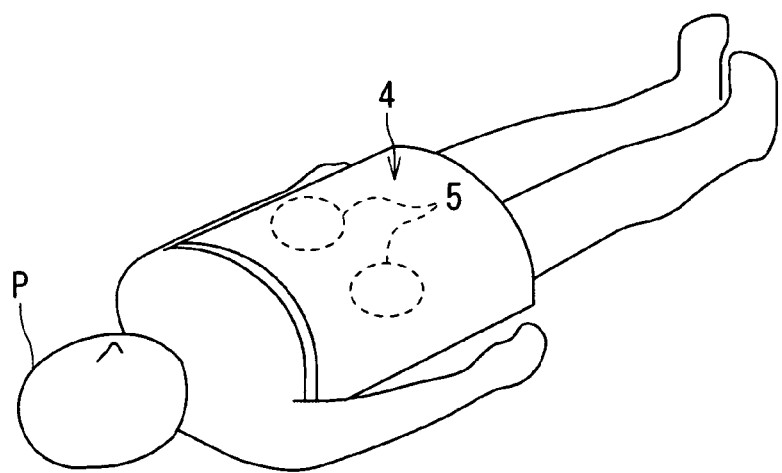
FIG. 6 illustrates a state in which the RF coil shown in FIG. 3 or 4 is placed on an object.

FIG. 6 illustrates a state in which the RF coil 4 shown in FIG. 3 or 4 is placed on an object.

As illustrated in FIG. 6, the RF coil 4 having a U shape in cross section shown in FIG. 3 or 4 is positioned adjacent to a body surface side of the object. NMR signals produced within the object can be received by the coil elements 5 of the RF coil 4.

Further, in FIG. 1, an example of the MRI apparatus 1 that includes the plurality of RF coils 4 each having two coil elements 5 is illustrated. However, the MRI apparatus 1 can include various kinds of RF coils 4 for wireless communications, each of the RF coils 4 having a larger number of coil elements 5. Also in this case, the MRI apparatus 1 can have the unique information generator 9 and the switch 10.

Figure 7:
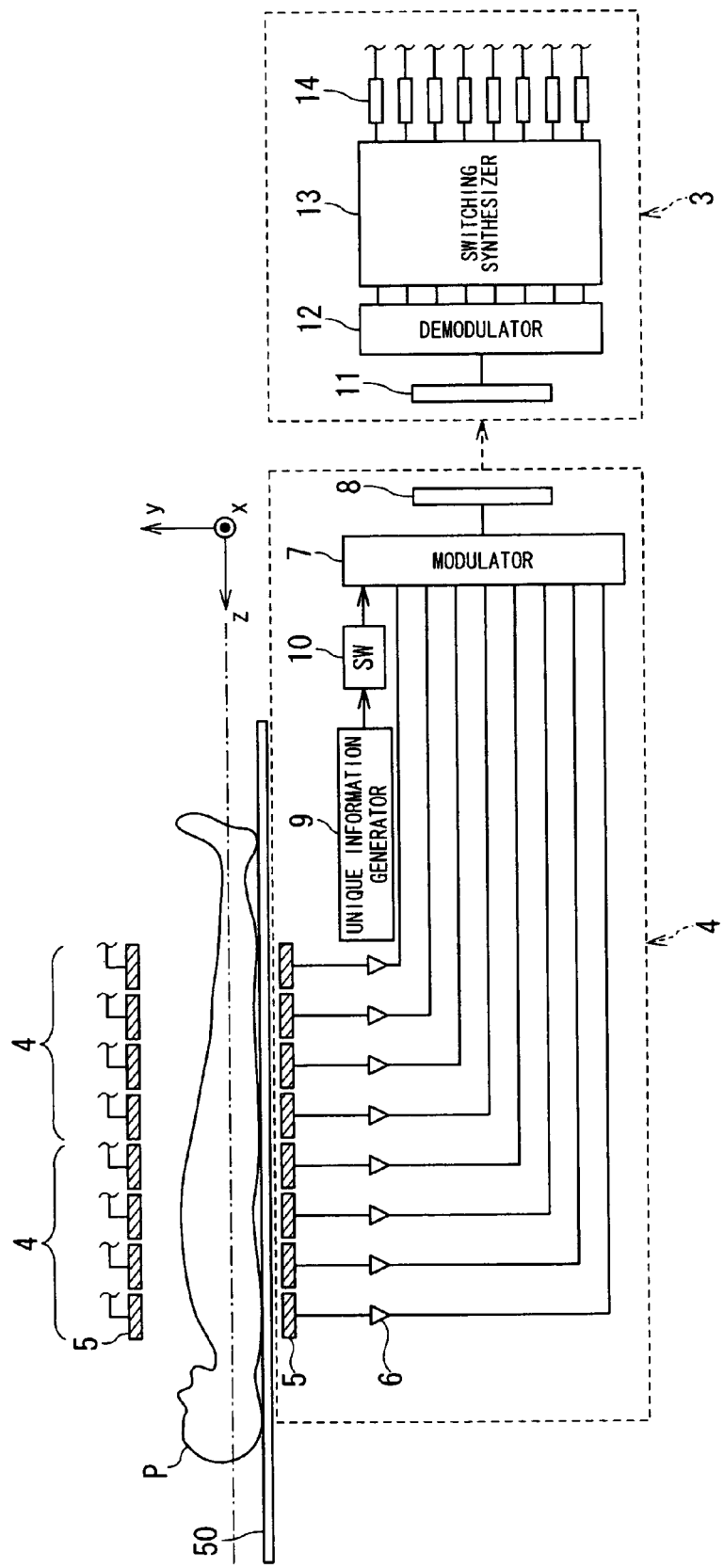
FIG. 7 illustrates another configuration example of the RF coils shown in FIG. 1.
Figure 8:
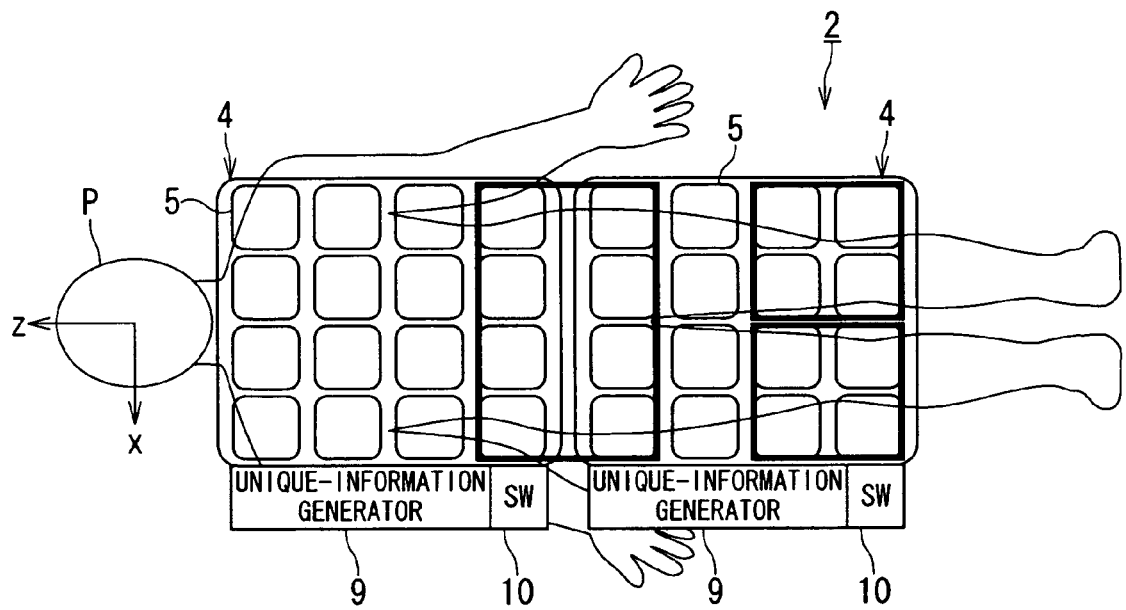
FIG. 8 illustrates an example of arrangement of coil elements shown in FIG. 7 set adjacent to a body surface side of the object.
Figure 9:
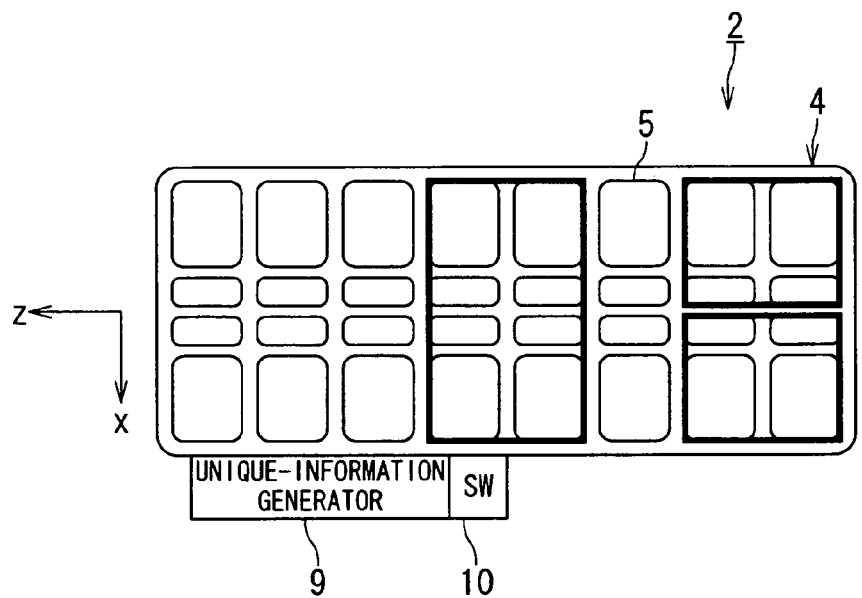
FIG. 9 illustrates an example of arrangement of coil elements shown in FIG. 7 set adjacent to a body back side of the object.

FIG. 7 illustrates another configuration example of the RF coils 4 shown in FIG. 1. FIG. 8 illustrates an example of arrangement of the coil elements 5 shown in FIG. 7 set adjacent to a body surface side of an object P. FIG. 9 illustrates an example of arrangement of the coil elements 5 shown in FIG. 7 set adjacent to a body back side of the object P.

As illustrated in FIGS. 7, 8, and 9, the RF coils 4 can be set adjacent to a body surface side and a body back side of the object P placed on a patient couch 50. In the vicinity of the body surface side of the object P, two RF coils 4 can be positioned in the z-direction so as to cover a wide area of imaging target sections. Each of the two RF coils 4 positioned adjacent to the body surface side of the object P has four rows of coil elements 5 in each of the x-direction and the z-direction, i.e., has 16 coil elements 5 in total. Also in the vicinity of the body back side of the object P, the RF coil 4 having four rows of coil elements 5 in the x-direction and eight rows of coil elements 5 in the z-direction, i.e., 32 coil elements 5 in total can be positioned so as to cover a wide area of imaging target sections. In the RF coil 4 positioned adjacent to the body back side of the object P, in terms of improvement of sensitivity in consideration of the existence of a backbone of the object P, the coil elements 5 positioned in the vicinity of the body axis are smaller than the other coil elements 5.

The coil elements 5 belonging to each of the RF coils 4 are connected to the respective amplifiers 6. The amplifiers 6 are connected to the common modulator 7. The unique information generator 9 is provided for each of the RF coils 4. The unique information generators 9 are connected to the respective modulators 7 through the respective switches 10. Each of the modulators 7 is connected to the signal transmitting antenna 8. Reception signals from the coil elements 5 are amplified by the respective amplifiers 6 and are frequency-modulated into different frequencies by the modulator 7. The reception signals modulated into specific frequencies are converted into electromagnetic waves and transmitted from the signal transmitting antenna 8. When the switch 10 is in the ON state, the unique information signal generated by the unique information generator 9 is also frequency-modulated by the modulator 7 and superposed onto each of the reception signals, and the superposed signal is transmitted as an electromagnetic wave from the signal transmitting antenna 8.

The controller 3 includes the signal receiving antenna 11. The signal receiving antenna 11 is connected to the demodulator 12. The output side of the demodulator 12 is connected to the switching synthesizer 13. The output side of the switching synthesizer 13 is connected to the receiving circuits 14. The number of the receiving circuits 14 is equal to the number of reception channels. In the example illustrated in FIG. 7, the number of reception channels is equal to the number of the coil elements 5.

The reception signals and the unique information signal transmitted as electromagnetic waves are received by the signal receiving antenna 11 and demodulated into original frequencies before the frequency modulation by the demodulator 12. This allows the controller 3 to acquire the reception signals of the respective coil elements 5 such that the signals can be identified. That is, because the reception signals from the coil elements 5 are frequency-modulated into predetermined specific frequencies and then the reception signals are wirelessly transmitted, it can be identified which coil element 5 received each of the reception signals. The reception signals demodulated by the demodulator 12 are divided and combined into reception signals corresponding to the reception channels. The reception signals corresponding to the reception channels are output to the respective receiving circuits 14 and become a target for signal processing.

Note that the switching synthesizer 13 may be disposed in the RF coil 4, and the divided and combined reception signals corresponding to the reception channels may be wirelessly transmitted. However, when the switching synthesizer 13 is disposed in the controller 3, i.e., in the reception side of wireless communication, the replacement of the RF coil 4 is easier, so the flexibility for dividing and combining processing can be enhanced.

Figure 10:
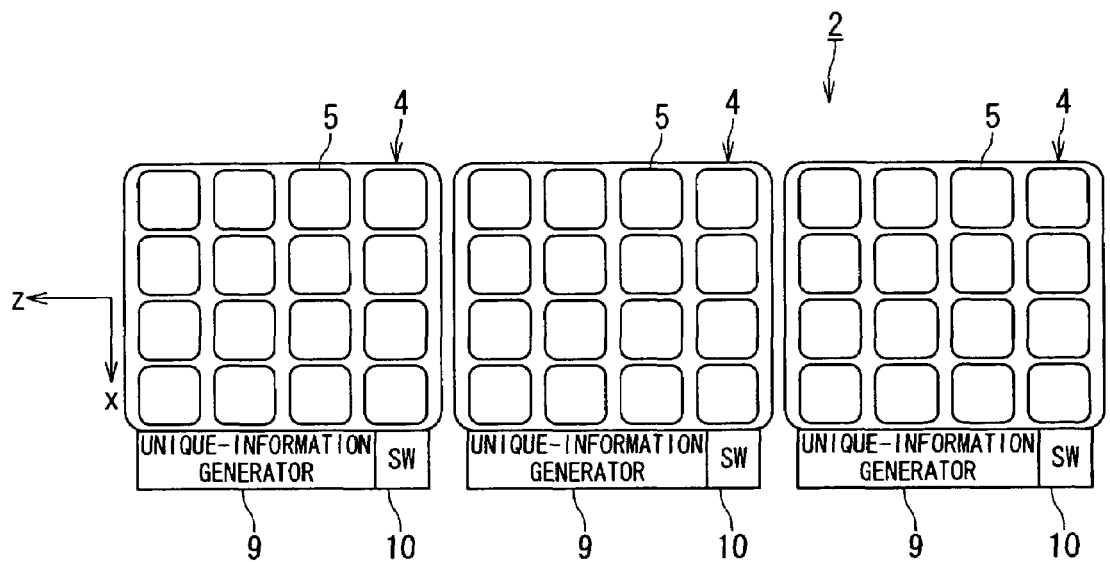
FIG. 10 illustrates another configuration example of the RF coils shown in FIG. 7 set adjacent to the body surface side of the object.
Figure 11:
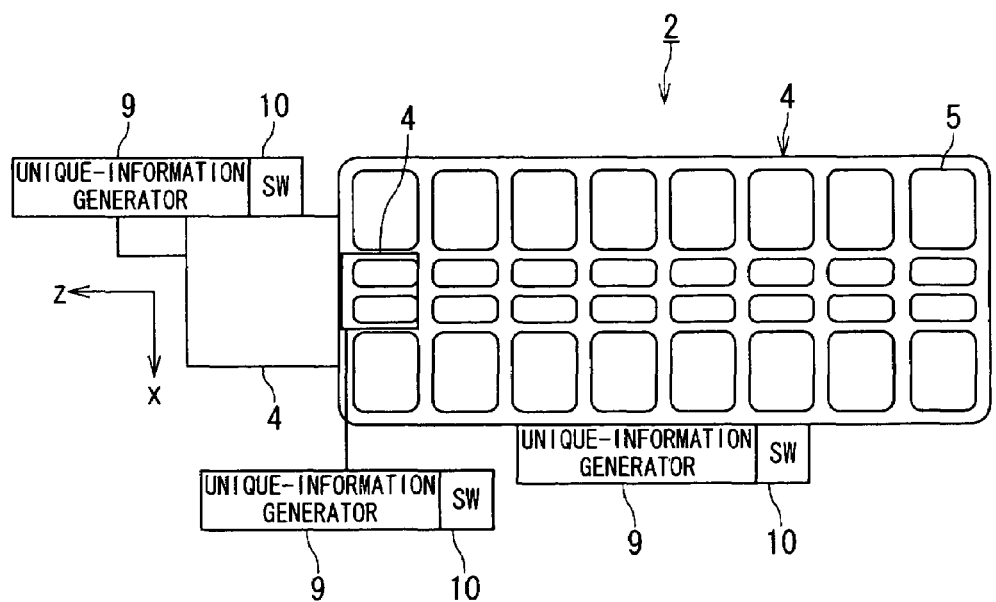
FIG. 11 illustrates another configuration example of the RF coils shown in FIG. 7 set adjacent to the body back side the object.

FIG. 10 illustrates another configuration example of the RF coils 4 shown in FIG. 7 set adjacent to the body surface side of the object P. FIG. 11 illustrates another configuration example of the RF coils 4 shown in FIG. 7 set adjacent to the body back side of the object P.

As illustrated in FIGS. 10 and 11, a larger number of RF coils 4 can be positioned in the vicinity of the object P. In an example illustrated in FIG. 10, the three RF coils 4, each having four rows of the coil elements 5 arranged in each of the x-direction and the z-direction, i.e., having 16 coil elements 5 in total, are arranged in the z-direction. That is, 48 coil elements 5 in total are positioned adjacent to the body surface side the object P. In an example illustrated in FIG. 11, the RF coil 4 having four rows of the coil elements 5 in the x-direction and eight rows of the coil elements 5 in the z-direction, i.e., 32 coil elements 5 in total is positioned adjacent to the backbone, the RF coil 4 having two coil elements 5 (not shown) is arranged in the vicinity of a jaw, and the RF coil 4 having 12 coil elements 5 (not shown) is arranged in the vicinity of the head. Therefore, 46 coil elements 5 in total are positioned adjacent to the body back side of the object P.

Each of the RF coils 4 includes the unique information generator 9 provided with the switch 10. Each of the coil elements 5 is connected to the dedicated amplifier 6 via a coil port (not shown). The unique information generator 9 and the amplifiers 6 are connected to the modulator 7.

An operation and an action of the MRI apparatus 1 will now be described below.

Figure 12:
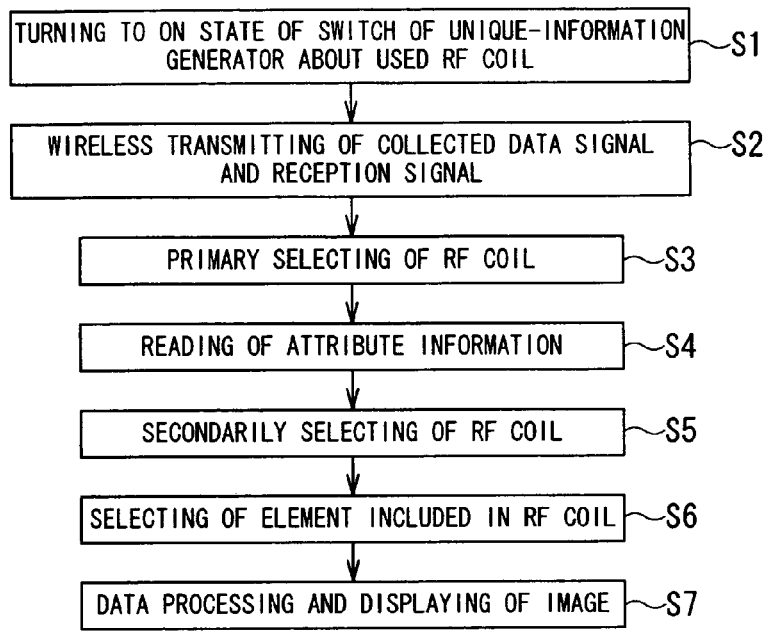
FIG. 12 is a flowchart of a procedure by which the MRI apparatus illustrated in FIG. 1 obtains an image of the object.

FIG. 12 is a flowchart of a procedure by which the MRI apparatus 1 illustrated in FIG. 1 obtains an image of the object. The reference characters of numerals appended to the letter "S" in FIG. 12 represent steps in the flowchart.

First, in step S1, before data collection is performed, a single or a plurality of RF coils 4 for use in data collection are positioned in the vicinity of imaging target sections of the object. Then, the switch 10 of the unique information generator 9 in each of the RF coils 4 for use in data collection is turned to the ON state, and the switch 10 of the unique information generator 9 in each of the other RF coils 4, which are not to be used for data collection, is turned to the OFF state. For example, when the RF coil 4 corresponding to the switch 10 of the unique information generator 9 being in the OFF state is to be used for data collection, the switch 10 is turned to the ON state in data collection. In contrast, when the RF coil 4 corresponding to the switch 10 of the unique information generator 9 being in the ON state is not to be used for data collection, the switch 10 is turned to the OFF state in data collection.

Note that switching the switch 10 for each of the RF coils 4 may be performed by an operator as occasion arises based on whether the RF coil 4 is to be used for data collection, or alternatively, may be performed by a programmable control in accordance with a scan plan previously established.

Next, in step S2, the data collection is performed. At this time, a reception signal is wirelessly transmitted from the RF coil 4 to the controller 3. Here, unique information unique to each of the RF coils 4 is unchanged for each of the RF coils 4, so the unique information is required to be transmitted to the controller 3 only once. Therefore, during data collection, the switch 10 turned to the ON state in step S1 may be switched to the OFF state. Alternatively, during data collection, the switch 10 being in the ON state in step S1 may be maintained by, for example, making the frequency of the reception data and the frequency of unique information associated with the reception data different (e.g., setting the frequency of unique information at a radio frequency).

An RF signal is transmitted from an RF coil for use in transmission (not shown) to the object under a static magnetic field, while a gradient magnetic field is formed in an imaging region by a gradient coil. An NMR signal produced by nuclear magnetic resonance within the object is received by the coil elements 5 included in the specified RF coil 4. The coil elements 5 output the NMR signals to the respective amplifiers 6 as reception signals being electrical signals. The reception signals amplified by the amplifiers 6 are frequency-modulated into predetermined frequencies by the modulator 7. In contrast, the unique information signal is output from the unique information generator 9 of the RF coil 4 corresponding to the switch 10 being in the ON state and is frequency-modulated by the modulator 7. The frequency-modulated reception signals for the respective coil elements 5 and the unique information signal are converted into electromagnetic waves and wirelessly transmitted from the signal transmitting antenna 8.

The wirelessly transmitted reception signals and the unique information signal are received by the signal receiving antenna 11 of the controller 3 and demodulated by the demodulator 12. The thereby generated reception signals, each being an electrical signal for each of the coil elements 5, are output to the switching synthesizer 13 while being overlaid with the unique information signal. The switching synthesizer 13 generates reception signals corresponding to the reception channels by performing the dividing and combining processing on the plurality of reception channels corresponding to the coil elements 5. Here, the reception signals from the coil elements 5 are made to be reception signals corresponding to the reception channels without being processed.

The reception signals output from the switching synthesizer 13 are digitized by the respective receiving circuits 14 through predetermined signal processing. The reception data output from each of the receiving circuits 14 is output to the RF coil primary selecting unit 19 of the computer 15.

Then, in step S3, the RF coil primary selecting unit 19 receives reception data with unique information and reception data without unique information from the receiving circuits 14. The RF coil primary selecting unit 19 selects only the reception data with the unique information from among all the reception data, and outputs the unique information to the attribute information acquiring unit 20 and outputs the reception data with the unique information to the RF coil secondary selecting unit 21.

The attribute information acquiring unit 20 acquires the attribute information by referring to the correspondence table illustrated in FIG. 2 based on the unique information input from the RF coil primary selecting unit 19. When acquiring the attribute information on the RF coil 4, the attribute information acquiring unit 20 then outputs information indicating that the attribute information on the RF coil 4 has been recognized to the interface unit 24. In response to this, the interface unit 24 displays information that inquires about whether the attribute information on the RF coil 4 is to be read or not on the monitor 17.

Then, in step S4, the attribute information on the RF coil 4 is read and displayed on the monitor 17. More specifically, the operator sees the monitor 17 and provides the interface unit 24 with an instruction to read the attribute information on the RF coil 4 by operating the input device 16. In response to this, the interface unit 24 displays the attribute information on the RF coil 4 input from the attribute information acquiring unit 20 on the monitor 17.

Then, in step S5, a specific RF coil 4 for use in image generation is secondarily selected. More specifically, when the operator sees the monitor 17 and provides the interface unit 24 with selection information on the specific RF coil 4 for use in data collection for image generation by operating the input device 16, the interface unit 24 outputs the selection information on the specific RF coil 4 to the RF coil secondary selecting unit 21.

Then, in step S6, a specific coil element 5 for use in image generation is selected from the specific RF coil 4. More specifically, when the operator sees the monitor 17 and provides the interface unit 24 with selection information on the specific coil element 5 for use in data collection for image generation by operating the monitor 17, the interface unit 24 outputs the selection information on the specific coil element 5 to the element selecting unit 22.

Then, in step S7, the reception data is subjected to data processing, and an image generated by the performance of the data processing is displayed on the monitor 17. More specifically, the RF coil secondary selecting unit 21 extracts the reception data with the unique information on the specific RF coil 4 from among the reception data with unique information selected by the RF coil primary selecting unit 19 based on the selection information on the specific RF coil 4 input from the interface unit 24. The RF coil secondary selecting unit 21 outputs the extracted reception data to the element selecting unit 22.

Subsequently, the element selecting unit 22 extracts the reception data transmitted from the specific coil element 5 from the reception data input from the RF coil secondary selecting unit 21 based on the selection information on the specific coil element 5 input from the interface unit 24. Therefore, only the reception data from the specific coil element 5 contained in the specific RF coil 4 for use in data collection is extracted. The extracted reception data is output to the data processing unit 23.

In response to this, the data processing unit 23 generates image data by performing the image reconstruction processing, such as the Fourier transform processing, and other necessary image processing on the reception data input from the element selecting unit 22. Then, the generated image data is displayed on the monitor 17. Because the image reconstruction processing and the image processing are selectively performed on only the necessary reception data, an increase in the amount of data processing can be suppressed and the data processing can be completed in a shorter time.

Note that, the unique information on the primary selected RF coil 4 may be maintained in a unit such as the RF coil secondary selecting unit 21 as long as the operator continues obtaining an image without replacing the RF coil 4 for use in data collection. In contrast, when the operator replaces the RF coil 4 for use in data collection with another RF coil 4 and provides an instruction to newly select a different RF coil 4 to the RF coil secondary selecting unit 21 from the input device 16 through the interface unit 24, the unique information on the RF coil 4 maintained in the RF coil secondary selecting unit 21 may be updated with the unique information on the newly selected RF coil 4.

In addition to the attribute information on the RF coil 4, the selection information on the RF coil 4 and the coil element 5 can be displayed on the monitor 17. In this case, image information indicating that which RF coil 4 and coil element 5 have been selected is supplied from the interface unit 24 to the monitor 17.

Figure 13:
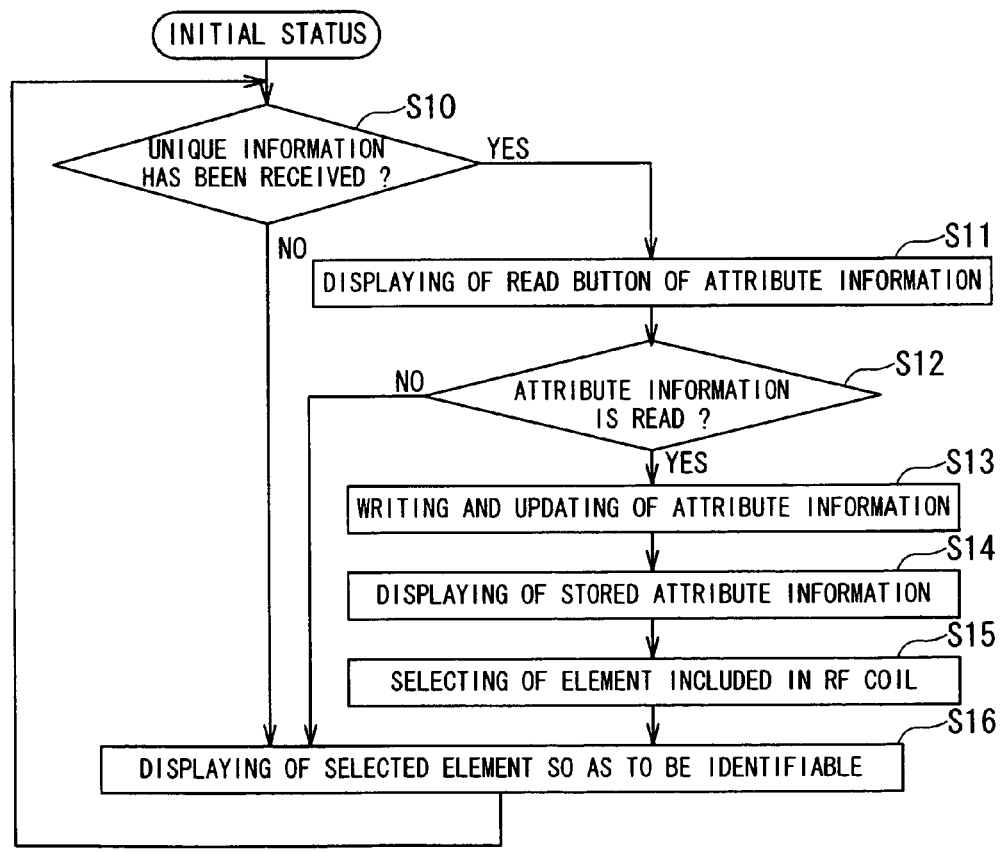
FIG. 13 is a flowchart of a process for reading unique information on an RF coil and displaying selection information on the RF coil and coil element on a monitor in a computer shown in FIG. 1.

FIG. 13 is a flowchart of a process for reading the attribute information (the unique information and the attribute information) on the RF coil 4 and displaying the selection information on the RF coil 4 and the coil element 5 on the monitor 17 in the computer 15 shown in FIG. 1. The reference characters of numerals appended to the letter S in FIG. 13 represent steps in the flowchart.

In the initial state, the attribute information acquiring unit 20 refers to the correspondence table illustrated in FIG. 2 via the RF coil primary selecting unit 19 in the computer 15 and recognizes the attribute information on an RF coil 4. Then, in step S10, the attribute information acquiring unit 20 determines that the unique information on the RF coil 4 has been received and outputs information indicating that the attribute information on the RF coil 4 has been recognized to the interface unit 24. Then, in step S11, the interface unit 24 displays a button as a trigger of reading of the attribute information used for instructing reading of the attribute information on the RF coil 4 on the monitor 17. In contrast, in step S10, when the attribute information acquiring unit 20 does not determine that the unique information has been recognized, the reading button as the trigger of reading of the attribute information is not displayed on the monitor 17.

Figure 14A:
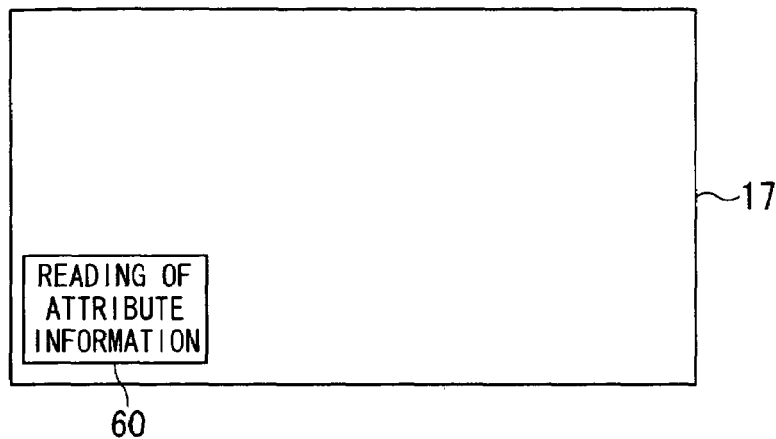
FIGS. 14A, 14B, and 14C are respectively an example of a screen appearing on the monitor shown in FIG. 1 in chronological order.
Figure 14B:
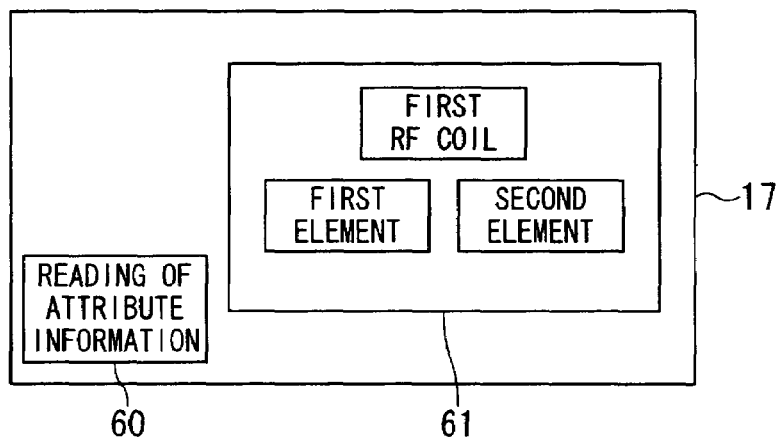
Figure 14C:
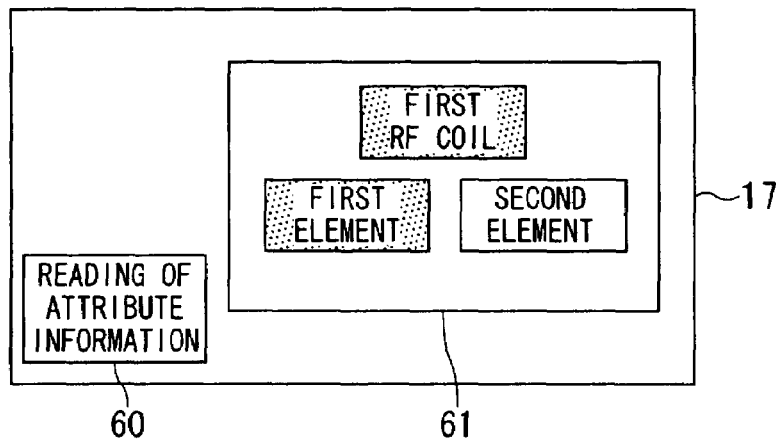

FIGS. 14A, 14B, and 14C respectively illustrate examples of a screen appearing on the monitor 17 shown in FIG. 1 in chronological order.

As illustrated in FIG. 14A, a reading button 60 is displayed on an operation screen of the monitor 17.

When the operator presses the button 60 as the trigger of reading of the attribute information by operating the input device 16 (e.g., a mouse), in step S12 of FIG. 13, the interface unit 24 determines that an instruction to read the attribute information on the RF coil 4 has been provided.

Next, in step S13, the interface unit 24 outputs an instruction to update the attribute information on the RF coil 4 to the RF coil secondary selecting unit 21. Then, the RF coil secondary selecting unit 21 receives the attribute information on the RF coil 4 from the interface unit 24 and maintains that attribute information. When there is attribute information on the RF coil 4 maintained in the RF coil secondary selecting unit 21, the attribute information is updated with new one.

In step S14, the interface unit 24 displays the attribute information on the RF coil 4 on the monitor 17. Therefore, as illustrated in FIG. 14B, the attribute information (the unique information and the attribute information) 61 on the RF coil 4 currently available for use in obtaining an image is displayed on the operation screen of the monitor 17. More specifically "first RF coil" as the unique information accompanying the reception data acquired from the RF coil 4 and "the number: 2", "arrangement of coil elements 5: first element (first coil element) and second element (second coil element) arranged in one row in the x-direction" as the unique information can be viewed on the operation screen of the monitor 17.

Then, in step S15 of FIG. 13, when the operator selects the first coil element, which is the coil element 5 for use in data collection, by operating the input device 16 (e.g., a mouse), the interface unit 24 outputs selection information on the coil element 5 indicating that the first coil element has been selected to the element selecting unit 22. This enables the element selecting unit 22 to extract reception data from the selected coil element 5 to use the reception data in data collection.

In step S16, the interface unit 24 provides the monitor 17 with an instruction to display the first coil element in an identifying manner such that selection of the first coil element can be visually identified. As a result, for example, as illustrated in FIG. 14C, selected first coil element and the unique information "First RF coil", to which "First Element" belongs, are highlighted by a display technique, such as coloring or pattern displaying. Therefore, the operator can readily know the coil element 5 selected for data collection.

In step S12, when the Read Attribute button 60 is not pressed by the operator, identification of the previously selected coil element 5 is maintained. When the attribute information acquiring unit 20 recognizes the attribute information based on the unique information on the RF coil 4, the attribute information on the RF coil 4 is read and the selected coil element 5 is displayed in an identifying manner in a similar flow to the process from step S10.

That is, together with wireless transmission of a reception signal from the RF coil 4 to the controller 3, the above-described MRI apparatus 1 wirelessly transmits various kinds of attribute information on the RF coil 4 and corresponding unique information through desired modulation and decoding to the controller 3.

Therefore, according to the MRI apparatus 1, in the case where the plurality of RF coils 4 are positioned, even when the controller 3 receives reception signals from the RF coils 4, the RF coil 4 being the sources of each of the received reception signals can be identified based on the unique information.

In the MRI apparatus 1, the switch 10 for allowing on and off settings of transmission of the unique information on the RF coil 4 to be switched prior to obtainment of an image may be set on the RF coil 4 such that the unique information on the RF coil 4 is wirelessly transmitted only when the RF coil 4 is used for obtaining an image.

Therefore, according to the MRI apparatus 1, only the reception data from the RF coil 4 for use in data collection can be selectively and automatically used for data collection without analysis or recognition processing of the unique information itself by recognition of the attribute information corresponding to the unique information in the controller 3.

That is, if the switch 10 is not set and all the RF coils 4 wirelessly transmit their unique information to the controller 3 on all occasions, the unique information on the RF coils 4 that are not to be used for obtaining an image would also be transmitted to the controller 3. Thus, it is difficult for the controller 3 to automatically determine a reception signal from an RF coil 4 that is to be used for data collection, and it would be necessary to have reception channels corresponding to the coil elements 5 in the controller 3 in order to be able to receive reception signals from all the RF coils 4. Additionally, the necessity of having, in the controller 3, a circuit for processing a reception signal from an RF coil 4 that is not actually used for obtaining an image would arise. It would also be necessary for the controller 3 to acquire selection information about reception data from the operator in order to identify reception data from an RF coil 4 that is to be used for data collection.

In contrast to this, providing the RF coil 4 with the switch 10 for switching between on and off settings of wireless transmission of the unique information enables the controller 3 to automatically discriminate between a reception signal from the RF coil 4 for use in imaging and a reception signal from the RF coil 4 that is not to be used for imaging based on the presence or absence of unique information. That is, the controller 3 can discriminate between the RF coil 4 that is to be used for obtaining an image and the RF coil 4 that is not to be used for obtaining an image not only in data collection but also prior to data collection. Accordingly, in contrast to the foregoing description, in which unique information is wirelessly transmitted together with a reception signal, only the unique information may be wirelessly transmitted from the RF coil 4 and received by the controller 3.

Therefore, only reception data from a necessary RF coil 4 can selectively be a target for data processing, so an increase in the amount of information to be handled can be avoided. As a result, an increase in the time required for obtaining an image and a decrease in the stability caused by an increase in the size of circuitry set in the controller 3 can be prevented. Additionally, when the controller 3 stores and manages a single or combination of unique information from one or more specific RF coils 4, conditions suited for obtaining an image can be set more easily, and in addition to that, it can be expected that limitations of operations regarding the RF coil 4 can be known. It is expected that this leads to simplification of operations and improvement of imaging performance capabilities.

Even when a plurality of unique information corresponding to a plurality of RF coils 4 including an RF coil 4 that is not used is transmitted to the controller 3, the operator can determine whether or not to use reception data based on detailed attribute information corresponding to the unique information. In addition to the RF coil 4, the coil element 5 for use in data processing can be selected by the operator. Therefore, data processing can be performed in the controller 3 more efficiently.

A modification example of the above MRI apparatus 1 will now be described below.

Figure 15:
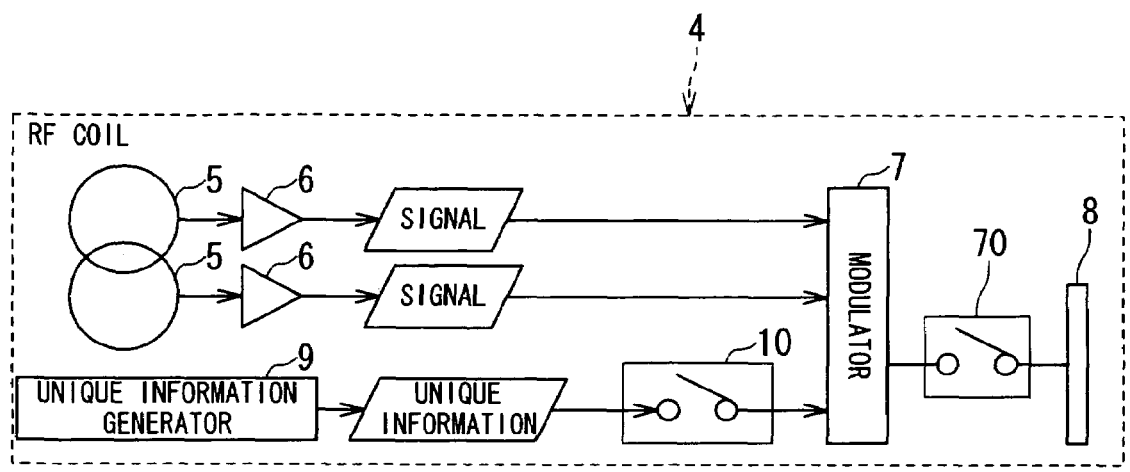
FIG. 15 is a block diagram of a modification example of one of the RF coils shown in FIG. 1.

FIG. 15 is a block diagram of a modification example of one of the RF coils 4 shown in FIG. 1.

As illustrated in FIG. 15, in addition to or as an alternative to the switch for switching between on and off settings of transmission of a unique information signal, a signal transmission selecting switch 70 for switching between on and off settings of wireless transmission of a reception signal from a desired RF coil 4 can be included. The signal transmission selecting switch 70 can be disposed at the output side of the modulator 7, for example. Alternatively, the signal transmission selecting switch 70 can be disposed at the output side of the coil element 5 or the amplifier 6.

When the signal transmission selecting switch 70 is disposed at the output side of the modulator 7, only a reception signal accompanied with the unique information can be wirelessly transmitted to the controller 3 by switching of the signal transmission selecting switch 70 between on and off settings and the switch for switching between on and off settings of transmission of a unique information signal. In this case, because reception signal received by the controller 3 is always accompanied with unique information, regardless of whether the unique information has been detected or not, the received reception signal can also be used for data processing.

In contrast, the provision of the signal transmission selecting switch 70 to the output side of the coil element 5 or the amplifier 6 enables switching of wireless transmission of a reception signal for each of the coil elements 5 to be performed by the RF coil 4 in a hardware manner.

According to the MRI apparatus 1 in the present embodiment, an image can be generated with a small amount of data processing by use of only reception data from an RF coil selected from among a plurality of RF coils 4. According to the MRI apparatus 1 in the present embodiment, an image can be generated with a smaller amount of data processing by use of only reception data from a coil element selected from among a plurality of coil elements.

Furthermore, according to the MRI apparatus 1 in the present embodiment, the RF coil 4 that is the source of each of the received reception data can be identified based on the attribute information corresponding to the attribute information, such as arrangement of the coil elements 5. Therefore, the data processing unit 23 can appropriately perform an image correction such as a luminance correction by using a correction value assigned to each of the RF coils 4.

What is claimed is:

1. A magnetic resonance imaging apparatus comprising:
a plurality of RF coils, each coil including at least one coil element and a unique information generator that generates unique information uniquely identifying a respectively associated coil and attributes associated therewith, each coil element being configured to receive nuclear magnetic resonance signals, and each said RF coil being configured to wirelessly transmit the received nuclear magnetic resonance signals and the unique information; and
a data processing control unit configured to receive the wirelessly transmitted nuclear magnetic resonance signals and unique information, and to generate image data based on the wirelessly received nuclear magnetic resonance signals in accordance with the wirelessly received unique information.

2. A magnetic resonance imaging apparatus according to claim 1, wherein each RF coil includes a switch configured to switch between on and off settings of wireless transmission of the unique information.

3. A magnetic resonance imaging apparatus according to claim 1, wherein each RF coil includes a switch configured to switch between on and off settings of wireless transmission of the unique information, and the switch is placed in a state of the off setting when the RF coil is connected to a battery charger.

4. A magnetic resonance imaging apparatus according to claim 1, wherein each RF coil includes:
a plurality of coil elements, and
a unit configured to respectively divide or combine reception signals from the coil elements.

5. A magnetic resonance imaging apparatus according to claim 1, wherein the data processing control unit stores additional unique information identifying attributes of each RF coil for use in data collection.

6. A magnetic resonance imaging apparatus according to claim 1, wherein the data processing control unit displays at least some of the wirelessly received unique information when receiving a display instruction.

7. A magnetic resonance imaging apparatus according to claim 1, wherein the data processing control unit, when receiving the unique information respectively received from a plurality of RF coils, generates the image data based on nuclear magnetic resonance signals received from an RF coil corresponding to unique information selected by an input device.

8. A magnetic resonance imaging apparatus according to claim 1, wherein each RF coil includes a plurality of coil elements, and the data processing control unit generates the image data based on nuclear magnetic resonance signals received from an RF coil corresponding to a coil element selected by an input device.

9. A magnetic resonance imaging apparatus according to claim 1, wherein the data processing control unit generates the image data using only received data accompanied with the unique information from among data received from the RF coils.

10. A magnetic resonance imaging apparatus according to claim 1, wherein each RF coil uses a unique coil identification ID) as at least part of the unique information.

11. A magnetic resonance imaging apparatus according to claim 1, further comprising:
a storage unit, in the data processing control unit, configured to store unique information including attribute information for each RF coil; and
an attribute information acquiring unit configured to acquire, from the storage unit, attribute information corresponding to received unique information acquired with the nuclear magnetic resonance signals,
wherein the data processing control unit generates the image data based on the nuclear magnetic resonance signals in accordance with the unique information and attribute information acquired by the attribute information acquiring unit.

12. A magnetic resonance imaging apparatus according to claim 11, wherein the attribute information includes at least one of:
(a) information indicating a use of the RF coil,
(b) information indicating a type of the RF coil,
(c) information indicating a shape of the RF coil, and
(d) information indicating an RF coil location.

13. An RF coil system comprising:
a unique information generating unit configured to generate unique information uniquely identifying a respectively associated coil and attributes associated therewith;
a coil element configured to receive nuclear magnetic resonance signals; and
a transmitting unit configured to wirelessly transmit the unique information and the nuclear magnetic resonance signals.

14. An RF coil system according to claim 13, wherein the unique information generating unit uses a unique coil ID of the RF coil as at least part of the unique information.

15. A magnetic resonance imaging method comprising:
generating unique information for each of plural RF coils uniquely identifying a respectively associated coil and attributes associated therewith;
generating nuclear magnetic resonance signals in each of at least one coil element of said RF coils;
receiving the unique information and the nuclear magnetic resonance signal within each said RF coil;
wirelessly transmitting the respectively associated nuclear magnetic resonance signals and the unique information away from each said RF coil; and
receiving the wirelessly transmitted nuclear magnetic resonance signals and unique information and generating image data based on received nuclear magnetic resonance signals in accordance with the received unique information.

16. The magnetic resonance imaging method according to claim 15, wherein the image data is generated using only wirelessly received data accompanied with wirelessly received unique information from among other wirelessly received nuclear magnetic resonance signal data.

17. The magnetic resonance imaging method according to claim 15, wherein a unique coil identification (ID) of an RF coil is used as at least part of the unique information.

* * * * *